(12) United States Patent
Chiu et al.

(10) Patent No.: US 9,656,080 B2
(45) Date of Patent: May 23, 2017

(54) SYMPATHETIC GANGLION STIMULATION METHOD FOR TREATMENT OF HYPERHIDROSIS, RAYNAUDS PHENOMENON, CEREBRAL ISCHEMIA, ASTHMA AND HYPERTENSION

(71) Applicants: Hung Wei Chiu, Taipei (TW); Ming Chien Kao, Taipei (TW); Mu Lien Lin, Taipei (TW)

(72) Inventors: Hung Wei Chiu, Taipei (TW); Ming Chien Kao, Taipei (TW); Mu Lien Lin, Taipei (TW)

(*) Notice: Subject to any disclaimer, the term of this patent is extended or adjusted under 35 U.S.C. 154(b) by 703 days.

(21) Appl. No.: 13/864,291

(22) Filed: Apr. 17, 2013

(65) Prior Publication Data

US 2013/0296977 A1 Nov. 7, 2013

Related U.S. Application Data

(60) Provisional application No. 61/625,830, filed on Apr. 18, 2012.

(51) Int. Cl.
*A61B 18/18* (2006.01)
*A61N 1/36* (2006.01)
(Continued)

(52) U.S. Cl.
CPC .......... *A61N 1/36117* (2013.01); *A61B 18/18* (2013.01); *A61F 7/12* (2013.01); *A61N 1/0551* (2013.01); *A61N 1/3606* (2013.01); *A61N 1/3611* (2013.01); *A61N 1/36139* (2013.01); *A61N 1/3787* (2013.01); *A61N 1/37252* (2013.01); *A61N 5/0601* (2013.01);
(Continued)

(58) Field of Classification Search
CPC ............ A61B 5/686; A61B 2560/0468; A61B 5/4076; A61B 18/18; A61B 2562/0209; A61B 5/04001; A61B 5/4047; A61B 5/42; A61B 5/4842; A61B 5/486; A61B 5/0031; A61B 5/0245; A61B 5/4836; A61B 2018/00434; A61B 2018/00642; A61B 2018/00702; A61B 5/00; A61B 5/4041; A61B 5/04; A61B 5/41; A61B 5/7271; A61N 1/0551; A61N 1/05; A61N 1/36139; A61N 1/3606; A61N 1/3605; A61N 1/36103; A61N 1/36135; A61N 1/36; A61N 1/40; A61N 1/36125; A61N 1/18; A61N 1/36057; A61N 1/36178; A61N 1/365; A61N 1/36128; A61N 1/36146; A61N 1/3615; A61N 1/3756; G06F 3/011; G06F 3/015
See application file for complete search history.

(56) References Cited

U.S. PATENT DOCUMENTS

2006/0116736 A1* 6/2006 DiLorenzo ........... A61N 1/0551
607/40

* cited by examiner

*Primary Examiner* — Deborah Malamud
(74) *Attorney, Agent, or Firm* — Opes IP Consulting Co.; Laurence Kao

(57) ABSTRACT

Methods for treatment of hyperhidrosis, Raynaud's phenomenon, cerebral ischemia and asthma and hypertension by nerve stimulation are disclosed. In particular, the invention relates to the improvement of these conditions by stimulating at least one ganglion selected from the group consisting of T-1 through T-4 ganglia, cervical ganglia, renal nerve or combinations thereof with an implantable, wireless, battery-less and lead-less stimulator. Stimulations of the ganglion may be carried out with pulsed radiofrequency, thermal energy or optical irradiation.

15 Claims, 9 Drawing Sheets

(51) Int. Cl.
*A61N 5/06* (2006.01)
*A61N 1/378* (2006.01)
*A61N 1/05* (2006.01)
*A61F 7/12* (2006.01)
*A61N 1/372* (2006.01)
*A61B 17/00* (2006.01)
*A61N 5/067* (2006.01)

(52) U.S. Cl.
CPC .......... *A61N 5/0613* (2013.01); *A61N 5/0622* (2013.01); *A61B 2017/00212* (2013.01); *A61B 2017/00221* (2013.01); *A61N 2005/067* (2013.01); *A61N 2005/0659* (2013.01)

PRF Waveform

Pulse freqency

Pulse Duration / pulse width

Continuous RF Waveform

Pulse width pulse rate / pulse frequecy

SYMPATHETIC GANGLION STIMULATION METHOD FOR TREATMENT OF HYPERHIDROSIS, RAYNAUDS PHENOMENON, CEREBRAL ISCHEMIA, ASTHMA AND HYPERTENSION

RELATED APPLICATIONS

This application is related to and claims priority to U.S. Provisional Application No. 61/625,830, filed on Apr. 18, 2012, entitled "Application of RF Chip Implant in Treating Primary Focal Hyperhidrosis and Related Conditions and Device Thereof," which is incorporated by reference herein in its entirety.

FIELD OF THE INVENTION

The invention relates to methods for treatment of hyperhidrosis, Raynaud's phenomenon, cerebral ischemia, asthma and hypertension by pulsed radiofrequency nerve stimulation. In particular, the invention relates to the improvement of these conditions by stimulating at least one ganglion selected from the group consisting of T-1 through T-4 ganglia, cervical ganglia, renal ganglia or combinations thereof with a wireless, battery-less and lead-less stimulator.

BACKGROUND OF THE INVENTION

Hyperhidrosis: Hyperhidrosis refers to profuse perspiration (excessive sweating) beyond the body's thermoregulatory needs. It is believed that an estimated 2-3% of Americans suffer from excessive sweating of the underarms (axillary hyperhidrosis) or the palms and soles of the feet (palmoplantar hyperhidrosis). For the purpose of discussion that follows, palmar hyperhidrosis (excessive sweating of the palms) will be stressed. Sweaty palms disorder is embarrassing, can hamper business interactions and cause social anxiety. Severe cases of palmar hyperhidrosis also have serious consequences, prohibiting people suffering from such a disorder to shake hands, lift any objects or work in professions that require contact with electricity.

Primary palmar hyperhidrosis is caused by overactivity of the sympathetic nervous systems, largely triggered by emotional stresses including anxiety, nervousness, anger and fear. Sympathetic nervous system is one of two major parts of the autonomic nervous system, the other being the parasympathetic system. In cases of palmar hyperhidrosis, the stellate ganglion and the first, second, third and forth thoracic ganglia of the sympathetic nerve chain are believed to play the major role in the abnormal signal generation to sweat glands of the palms.

There are various treatments available for palmar hyperhidrosis. Aluminum chloride is used in antiperspirants. However, patients suffered from hyperhidrosis require antiperspirants in high concentration to effectively treat the symptoms of the condition. Anticholinergic drugs have direct effect on sympathetic nervous systems although they have side effects. Botulinum injection on affected area may block neural control of sweat glands. However, such a treatment is expensive and short-term, with patients requiring to receive injection every 6 to 12 months.

Removal or destruction of sweat gland is one surgical option available for hyperhidrosis although such a treatment has many side effects. Endoscopic transthoracic sympathectomy (ETS), a minimally invasive surgical procedure, involves resection or clamping of the thoracic ganglion on the main sympathetic chain. Particularly, an en bloc ablation by laser vaporization of the T2 ganglion has proven to yield a permanent therapeutic effect for palmar hyperhidrosis. However, ablation of the targeted nerve cluster has a host of complications, including compensatory sweating, bradycardia, hypersensitive to light, lack of norepinephrine and acetylcholine, and possibly nerve regeneration. Clamping of the thoracic ganglion is intended to permit the reversal of the ablation procedure so as to minimize the aforementioned complications. However, it has shown that effective clamping also causes irreversible damages to the nerve, and patients continue to suffer similar side effects such as compensatory hyperhidrosis.

Electrical stimulation of the sympathetic nerve chain has been proposed to treat hyperhidrosis. The principle behind such approach involves disruption and modulation of hyperactive neuronal circuit transmission at specific sites in the sympathetic nerve chain. The procedure is also said to minimizes or possibly eliminate the complications from ETS. Currently, electrical stimulation of the nerve is usually carried out by surgically implanting a generator in the vicinity of the targeted nerve cluster, and then applying electrical modulation to the nerve through electrodes that are connected to the generator by lead. Conventional stimulation device, however, bears significant shortcomings. For example, the implantable generator requires a battery or power source, which means the size of the device cannot be too small. Also, an extension lead, containing electric wire, is attached to the generator and carries the electric pulses to the electrode that is attached to the nerves or tissues. This lead is undesirable as it may tangle with or disturb the nearby organs. If damaged, a leak and possibly more severe complications may occur as a result.

It is therefore the goal of the present invention to provide a treatment method for palmar hyperhidrosis by employing a miniature, battery-less stimulator that requires no extension lead.

Raynaud's phenomenon: Raynaud's phenomenon is a disorder of the blood vessels, usually in the fingers and toes. It is a condition in which cold temperature or emotional stress causes blood vessel spasms that block blood circulation to the fingers and toes. Specifically, Raynaud's phenomenon is a hyperactivation of the sympathetic nervous system causing extreme vasoconstriction of the peripheral blood vessels, lead to tissue hypoxia. Typical symptoms are pain within the affected extremities, discoloration, and sensations of cold and/or numbness. The disorder can be distressing and in severe cases, dangerous when someone with Raynaud's is placed in cold climate.

Treatment for Raynaud's phenomenon may include prescription medicines such as nifedipine or diltiazem, though it has the usual side effects of headache, flushing, and ankle edema. An ETS can be performed by ablating the nerves that signal the blood vessels of the fingertips to constrict. But complications common to ETS would also occur.

Cerebral ischemia: cerebral ischemia is a medical disorder where there is insufficient blood flow to the brain to meet metabolic demand. Typically ischemia occurs when one of the arteries that brings blood to a part of the brain is blocked by a blood clot or a cholesterol plague. The resulting lack of oxygen or cerebral hypoxia leads to death of brain cells or ischemic stroke. Cerebral ischemia is a leading cause of adult disability in the United States, killing nearly 150,000 people each year.

Tissue plasminogen activator (TPA) is an effective medication that lyses a clot and possibly restores blood circulation to the affected area of the brain. However, administering TPA has a very limited time window of only 3-4 hours. TPA also may not be suitable for patients with certain conditions, such as tendency to bleed, heart problems or diabetics, because there is the potential risk of serious brain bleed. Surgery, such as carotid endarterectomy, may also be performed on patients suffering from brain ischemia. The procedure aims to unlock carotid arteries, which supply blood to the brain, that have accumulated plaque or fat buildup in them. However, the inherent dangers of such surgical procedure prompt other safer and less invasive approach for the treatment of cerebral ischemia Asthma: Asthma is a chronic lung disorder that inflames and narrows the airways. The inner walls of an asthmatic's airways are swollen or inflamed. This swelling and inflammation makes the airways extremely sensitive to irritations and increases one's susceptibility to an allergic reaction.

Most asthma medications work by relaxing bronchospasm. Treatment is usually with an inhaled short-acting beta-2 agonist and oral corticosteroids. Side effects such as insomnia, anxiety, increased heart rate and tremor occur in some patients taking asthmatic medications.

Hypertension: Hypertension is a medical condition in which the blood pressure in the arteries is elevated. An elevation of blood pressure increases the risk of developing cardiac disease, renal disease, atherosclerosis or arteriosclerosis, eye damage and stroke. It is estimated that hypertension affects approximately one in three adults in the U.S., —73 million people—clearly a serious public health problem.

Abnormally elevated sympathetic nerve activity is found to contribute to the progression of hypertension and renal disease. Therefore, hypertension, renal and heart failure can be treated by reducing the sympathetic efferent or afferent nerve activity of the kidneys. Medication such as renninangiotensin system inhibitors, calcium channel blockers or diuretics have been used to treat hypertension.

The causes of the prevalent diseases discussed herein can all be related to abnormal activities of the sympathetic nerve chain. Therefore, novel methods of treating these diseases are presented to reduce the side-effects associated with the conventional approaches.

SUMMARY OF THE INVENTION

The present invention discloses methods of treating physiological disorders caused by abnormality of sympathetic activities by implanting a pulsed radiofrequency stimulator at specific locations along the sympathetic chain of the patient.

In an embodiment, the invention provides a method of treating hyperhidrosis, Raynaud's phenomenon, cerebral ischemia, asthma and hypertension by positioning an implantable, lead-less and battery-less stimulator proximate to at least one ganglion along the sympathetic nerve chain wherein the stimulator is configured to be wirelessly controlled and charged, monitoring the electrical states of the at least one ganglion and the stimulator, applying pulsed radiofrequency to the ganglion, and adjusting the stimulation parameters of the pulsed radiofrequency based on the monitored electrical states until the symptoms of the disease have been alleviated. For hyperhidrosis, Raynaud's phenomenon, cerebral ischemia and asthma, this involves positioning the stimulator proximate to the inferior portion of the stellate ganglion, and over T2-T4. For hypertension, this involves positioning the stimulator proximate to the renal ganglia.

According to the present invention, the stimulation parameters comprise pulse frequency, pulse width duration, current amplitude, voltage amplitude, duty cycle and waveform of the pulsed radio frequency. The electrical states of the ganglion comprise the bio-impedance of the ganglion being stimulated. The electrical states of the stimulator comprise voltage level, current amplitude, impedance and temperature of the stimulator.

In an embodiment, the method of treating hyperhidrosis, Raynaud's phenomenon, cerebral ischemia, asthma and hypertension further includes the step of monitoring the physiological states of a patient. The physiological states comprise heart rate, body and tissue temperatures, blood pressure and blood oxygen level of the patient. Based on the monitored physiological states, the stimulation parameters of the pulsed radiofrequency may be adjusted.

In an embodiment, the method of treating hyperhidrosis, Raynaud's phenomenon, cerebral ischemia, asthma and hypertension further includes the step of transmitting the monitored electrical and/or physiological states to a remote controller outside the patient body. The remote controller may adjust the stimulation parameters of the pulsed radiofrequency based on the monitored electrical and/or physiological states until the symptoms of the diseases have been alleviated. The remote controller may also be configured to wirelessly charge the stimulator.

In an embodiment, the invention provides a method of treating hyperhidrosis, Raynaud's phenomenon, cerebral ischemia, asthma and hypertension by positioning an implantable, lead-less and battery-less stimulator proximate to at least one ganglion along the sympathetic nerve chain wherein the stimulator is configured to be wirelessly controlled and charged. The method further involves applying thermal energy to the ganglion via the stimulator until the symptoms of the diseases have been improved.

In addition to the embodiments describe so far, the invention further provides a method of treating a disease of a human patient diagnosed with at least one of hyperhidrosis, Raynaud's syndrome, cerebral ischemia, asthma or hypertension by positioning an implantable, lead-less and battery-less stimulator proximate to at least one ganglion along the sympathetic nerve chain wherein the stimulator is configured to be wirelessly controlled and charged. The method further involves applying optical irradiation to the ganglion via the stimulator until the symptoms of the diseases have been alleviated.

DETAILED DESCRIPTION

In the following description, reference is made to the accompanying figures that form a part hereof, and in which are shown by way of illustration the several embodiments of the invention. It is to be understood that other embodiments are contemplated and may be made without departing from the scope or spirit of the present invention. The following disclosure is therefore not to be interpreted in a limiting sense. Rather, the scope of the invention is to be defined in accordance with the appended claims.

Novel method and apparatus have been developed to regulate sympathetic nerve activity to improve the conditions of a patient diagnosed with at least one of hyperhidrosis, Raynaud's phenomenon, cerebral ischemia, asthma or hypertension. Particularly, the method involves surgically implanting a wireless, battery-less and lead-less stimulator in the proximity of at least one ganglion along the sympathetic nerve chain, and applying pulsed radiofrequency (PRF) stimulations to the targeted ganglion until the symptoms are improved.

Figure 1:
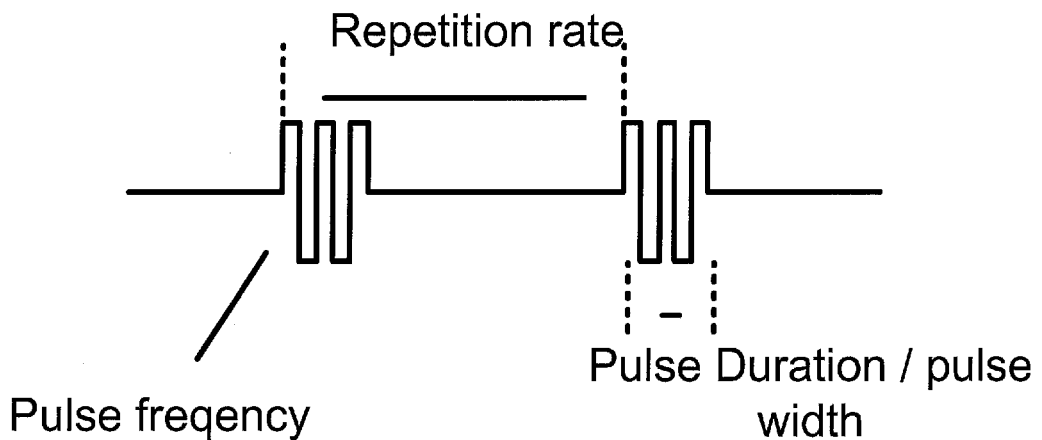
FIG. 1 compares the pulsed radiofrequency waveform with the continuous radiofrequency waveform.
Figure 1:
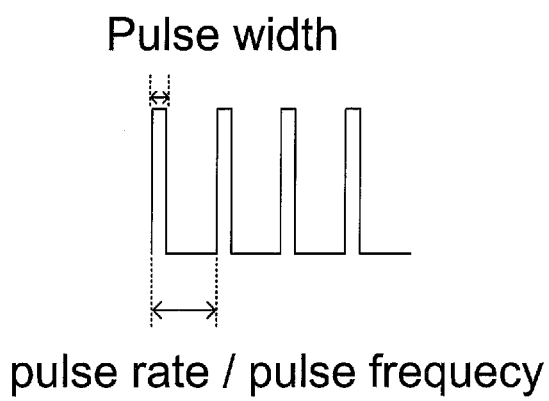

The efficacy of PRF treatment in nerve disorders has been well documented. In general, there are two types of PRF procedures. The first involves applying continuous radiofrequency (RF) to the targeted tissue, while the other involves using PRF. Biological changes in tissue during electrical stimulation can occur due to thermal effects, the high intensity electric fields, or as a result of both. PRF applies short pulses of RF signals from a pulse generator to the tissue. The heat produced during these pulses depends on the power deposition. In PRF, because the pulse duration is only a small percentage of the time between pulses, the average tissue temperature rise for the same RF voltage is much less for PRF than for continuous RF, as illustrated in FIG. 1. Thus, higher voltages can be applied in a PRF procedure than are commonly used in RF without raising the tissue temperature into the denaturation range above 45° C. Recent studies also suggest that PRF operating at high frequency with sinusoidal waveform can better reduce thermal damage to the nerve, as compared to RF stimulation.

The sympathetic nervous system (SNS) is part of the autonomic nervous system, which also includes the parasympathetic system. The SNS activates the flight-or-fight response, and operates through a series of interconnected neurons.

There are two kinds of neurons involved in the transmission of any signal through the SNS: pre- and post-ganglionic. Sympathetic neurons of the spinal cord (or preganglionic neurons) communicate with peripheral sympathetic neurons (or postganglionic neurons) via a series of sympathetic ganglia. Within the ganglia, preganglionic neurons join postganglionic neurons through chemical synapses. At synapses within the sympathetic ganglia, preganglionic sympathetic neurons release acetylcholine, a chemical messenger (or neurotransmitter) that binds and activates nicotinic acetylcholine receptors on postganglionic neurons. And in response, postganglionic neurons (with two notable exceptions) release noradreanline, which activates adrenergic receptors on the peripheral tissues.

The exceptions mentioned above are postganglionic neurons of sweat glands and chromaffin cells of the adrenal medulla. Postganglionic neurons of sweat glands release acetylcholine for the activation of muscarinic receptors. Chromaffin cells, act like postganglionic neurons, synapse with preganglionic neurons and stimulate the chromaffin to release norepinephrine and epinephrine directly into the blood.

Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axon (or nerve fiber), is a long, slender projection of a nerve cell, or neuron, that typically connects electrical impulses away from the neuron's cell body. Axon of the sympathetic nerves leave the spinal cord in ventral branches (rami) of the spinal nerves, and then separate out as "white rami" which connects to two ganglia extending alongside the vertebral column on the left and right.

The axons of the autonomic nerve cells in the nuclei of the cranial nerves, in the thoracolumbar lateral comual cells, and in the grey matter of the sacral spinal segments are called preganglionic sympathetic nerve fibers, while those in ganglion cells are termed postganglionic sympathetic nerve fibers. The postganglionic sympathetic nerve fibers converge in ganglia that are located alongside the vertebral bodies in the neck, chest, and abdomen. Specifically, the stellate ganglion is located laterally adjacent to the intervertebral space between the seventh cervical and first thoracic vertebrae. The first, second third and forth thoracic ganglia lie next to their respective vertebral bodies on either side of the thoracic cavity.

Physiological disorders associated with abnormal sympathetic nerve activity may be treated with electrical stimulation of the appropriate ganglia outside of the spinal column. In the present invention, the preferred effect is to use an implantable stimulator to modulate nerve activities with pulsed radiofrequency (PRF). Reference of the term "stimulate" or "stimulation" in this disclosure means application of PRF signal that may be either excitatory or inhibitory to a sympathetic ganglion affected by such signal. Proper PRF stimulation prevents the total destruction of the ganglion, thereby offers the advantage over the irreversible en bloc ablation procedure.

As used herein a stimulator is positioned "proximate to" or "in the proximity of" a sympathetic ganglion means a stimulator placed at a site capable of producing a direct PRF effect on tissue that if stimulated would result in the alleviation of the diseases' symptoms. By way of an example, a stimulator may be placed either directly on the tissue or about 10 mm or less from the tissue.

As use herein "adjusting stimulation parameters of pulsed radiofrequency" means adjusting pulse frequency, pulse width duration, current amplitude, voltage amplitude, repetition rate, duty cycle and/or pulse waveform of the pulsed radiofrequency.

A variety of approaches are available for upper thoracic implantation of stimulator. The common procedures are: posterior paravertebral thoracic sympathectomy, thoracoscopic sympathectomy and retroperitoneal lumbar sympathectomy. The preferred implantation method of the present invention is accomplished percutaneously using an endoscope system.

Figure 2:
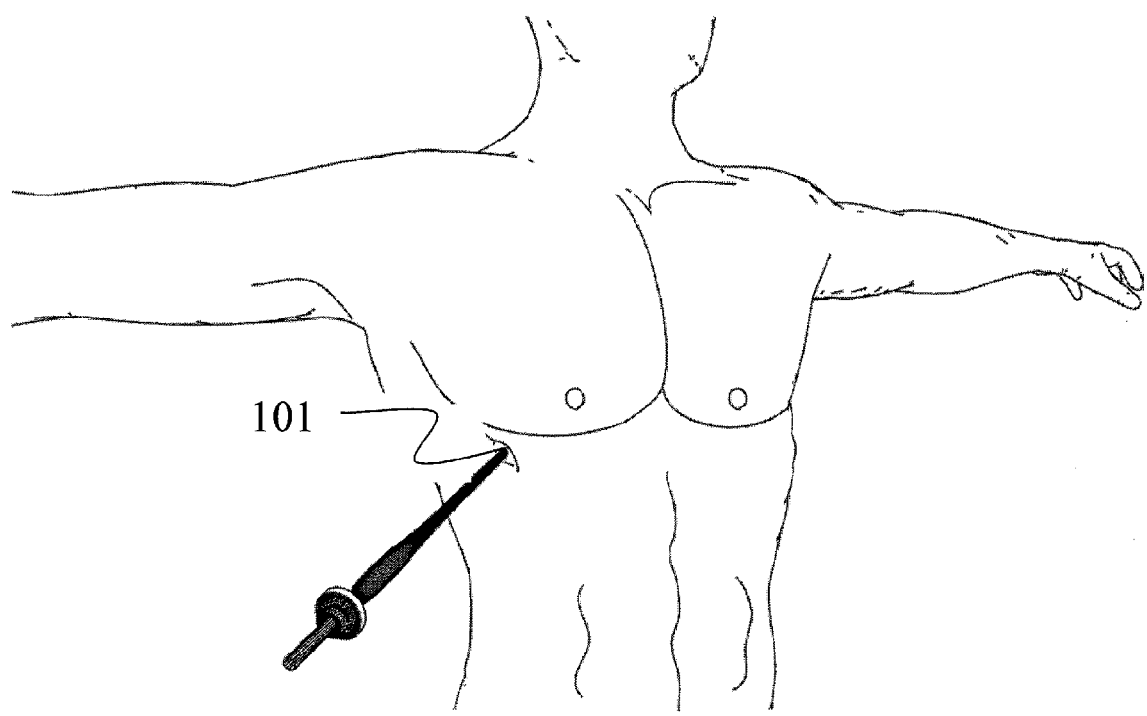
FIG. 2 is a schematic illustration of a patient having an endoscopic insertion site in the second or third intercostals space at the anterior axillary line.
Figure 3:
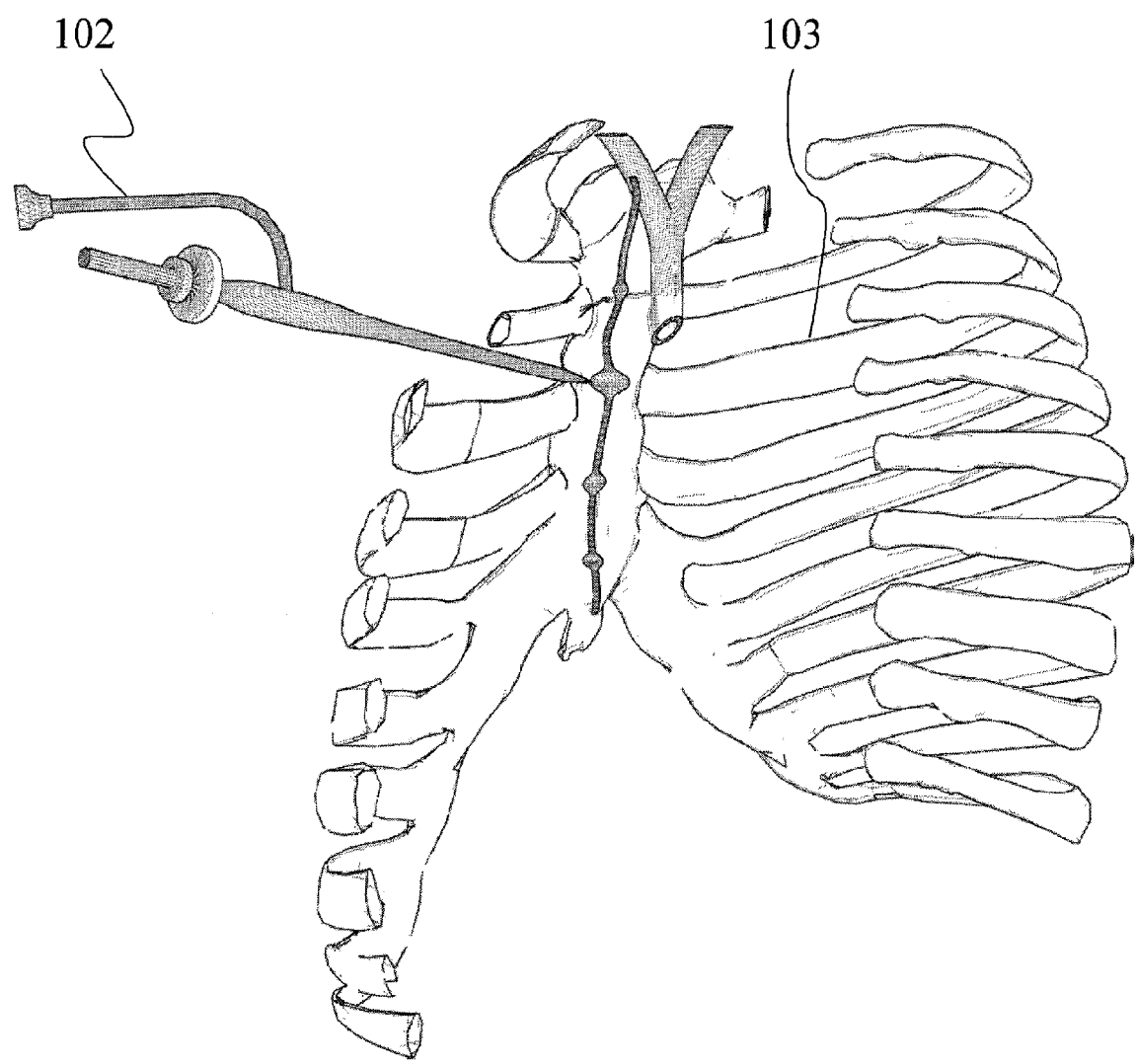
FIG. 3 is a partial exposed view of the hemithorax displaying the endoscopic system incising the parietal pleura to expose the sympathetic nerve chain.

The implanting procedure starts with placing the patient under general anesthesia and intubated with a double lumen endotracheal tube. The double lumen endotracheal tube allows alternating one-lung ventilation. A single micro incision, preferably no longer than 5 mm, is made in the second or third intercostals space at the anterior axillary line that is identified as insertion site 101, as shown in FIG. 2. Now referring to FIG. 3, a 5 mm-diameter endoscope 102 is inserted through the insertion site 101 into the thoracic cavity 103. Identification of the first and second ribs, the targeted ganglia (T1-T4), the azygos vein, the brachiocephalic and subclavian arteries, and the parietal pleura is performed. The sympathetic nerve chain is visualized as the ganglionated, longitudinal cord structure located at the junction of the ribs and the vertebral bodies.

Figure 4:
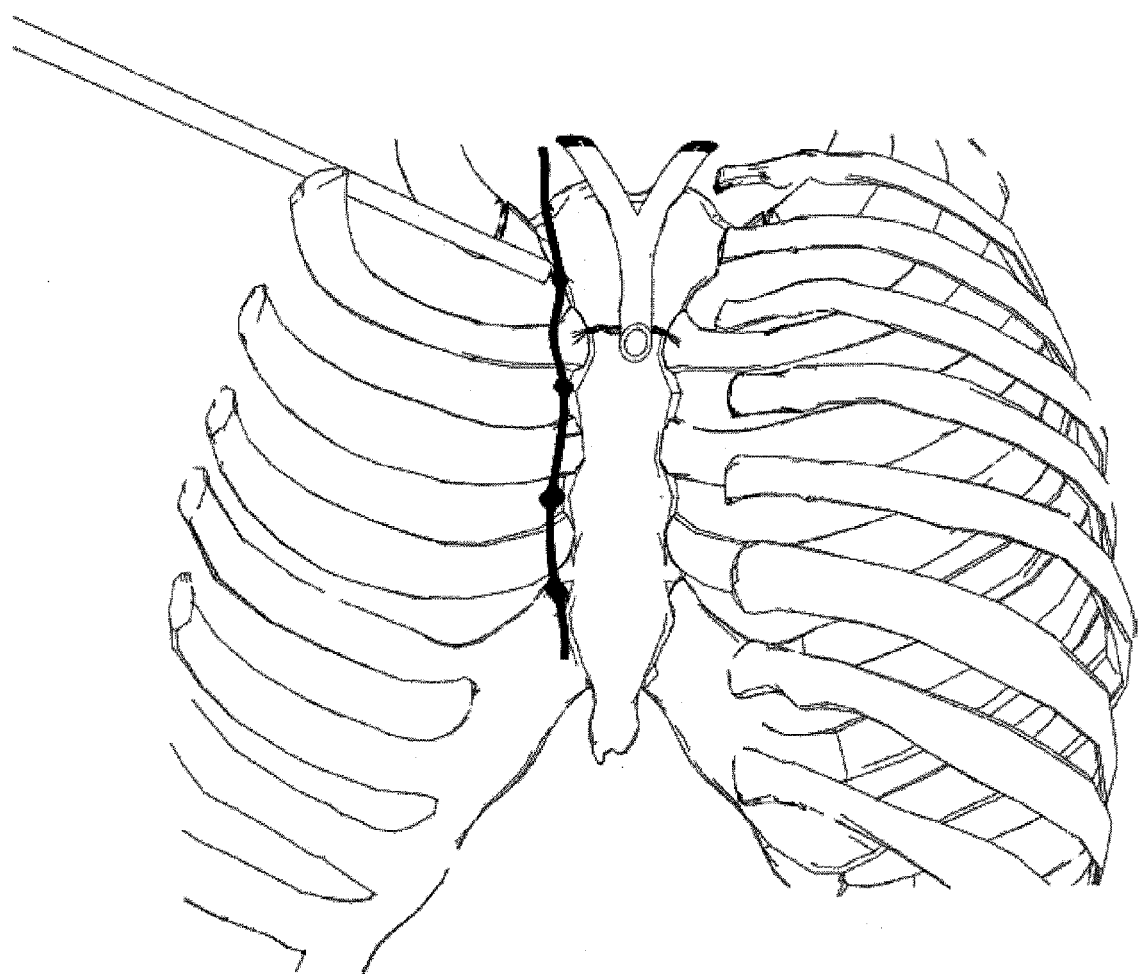
FIG. 4 is an expose view of the thoracic ganglia with the implantable stimulator positioned for pulse radiofrequency treatment.
Figure 5:
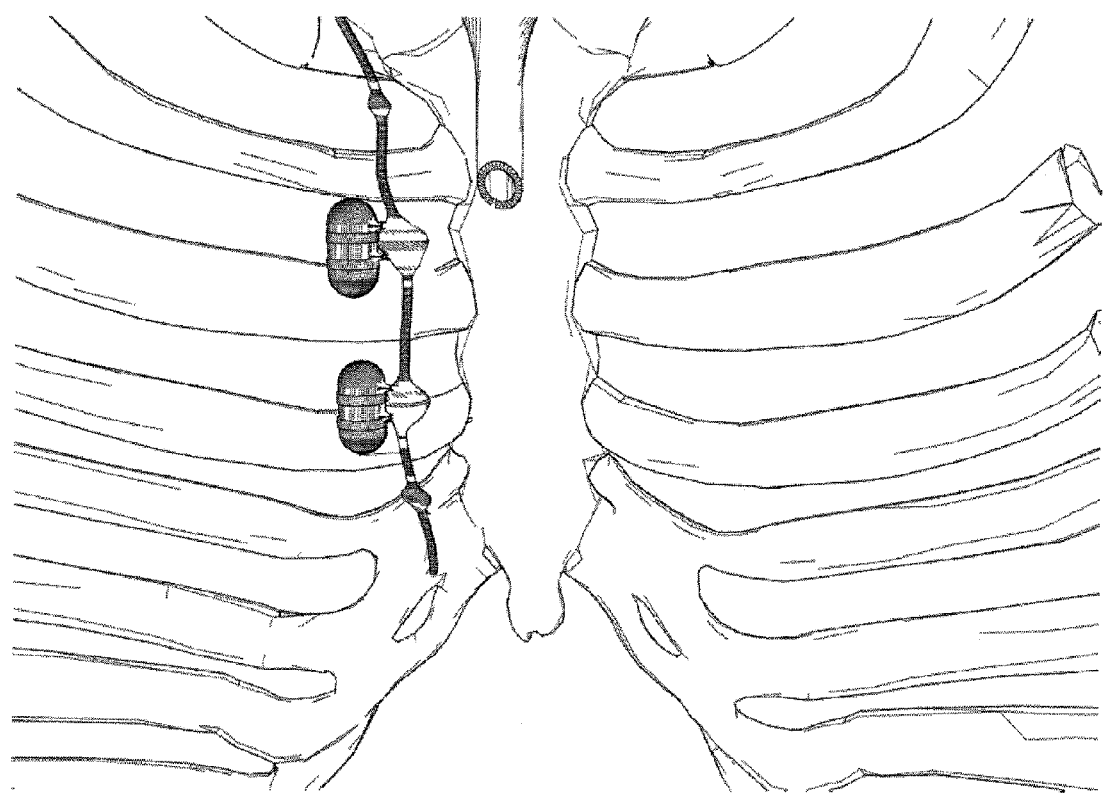
FIG. 5 illustrates implantable stimulators sutured on targeted sympathetic ganglion.

A wireless, battery-less and lead-less stimulator capable of generating PRF is then inserted via the insertion site 101 to a predetermined location along the sympathetic nerve chain that is associated with the physiological disorder being treated, as shown in FIG. 4. For palmar hyperhidrosis, the stimulator is preferably placed in the proximity of the T2 and T3 ganglia. Palmar skin perfusion (PSP) and palmar skin temperature (PST) of the patient are monitored to verify that the correct ganglion is being stimulated. The stimulation parameters of the PRF may be further adjusted by the stimulator itself or wirelessly by a separate remote controller until proper PSP and PST responses are received. Once the symptom of the disorder is improved, the stimulator may be directly sutured or clamped to the nearby tissue or parietal pleura, as shown in FIG. 5. Because the stimulator of the present invention is lead-less, the operating surgeons need not be concerned with lead migration or lead direction out of thoracic cavity as found in the prior art methods. Because the stimulator is further configured to be wirelessly powered, there is also no concern with power cable. Implanting an entirely stand-alone stimulator significantly simplifies and shortens the surgical procedure. A topical skin adhesive is used to close the tiny single incision after the stimulator is sutured or affixed. Upon completion of one side of the body, the other side is then done in similar fashion.

The stimulator employed in the present invention may also comprise an electrical sensor means that monitor electrical states of the ganglion and the stimulator. For example, impedance magnitude may be determined by the stimulator due to tissue regeneration of the stimulated ganglion or electrode encapsulation. Circuit parameters may be regulated internally by the stimulator's preprogrammed rules. The stimulator may also comprise a physiological sensor means that monitor the physiological states of the patient. Physiological factors such as body and tissue temperatures, heart rate, blood pressure or blood oxygen level of the patient may be determined. Accordingly, the treatment method of the present invention may further include a step of monitoring the electrical states of the ganglion and the stimulator. A further step of monitoring the physiological states of the patient may also be preformed. According to the monitored states, another step of adjusting the stimulation parameters of the PRF may be undertaken until the symptoms of the diseases are demonstrably relieved.

Electrical nerve stimulation involves applying an energy signal (pulse) at a certain frequency to the neurons of a nerve. The energy signal causes depolarization of neurons inside the nerve above the activation threshold, resulting in an action potential. The energy applied is a function of the current/voltage amplitude and pulse width duration. In the present invention, to effectively treat the aforementioned physiological disorders, the current/voltage amplitude of the PRF may be operated at a voltage between 1 volt and 60 volts. Preferably, PRF is applied at a low amplitude of 5 volts in sinusoidal waveform to stimulate the targeted ganglion without irreversibly damaging the nerve. The pulse frequency may be in the range of 10 KHz to 10 MHz, preferably set at 500 KHz. Repetition rate of the PRF may be operated at between 0.1 Hz and 10 Hz, preferably at 2 Hz. Pulse width duration is between about 0.1 ms and 500 ms, preferably set at 50 ms. These PRF parameters ranges are generally found to be effective in treating disorders such as hyperhidrosis, Raynaud's phenomenon, cerebral ischemia, asthma and hypertension.

An alternative embodiment of the present invention involves using thermal energy to stimulate at least one ganglion along the sympathetic nerve chain until the symptoms of the diseases are demonstratively alleviated. Particularly, a stimulator capable of applying thermal stimulation is percutaneously implanted in the proximity of the targeted ganglion. The stimulator may include thermal means that can produce a "cooling effect" on the sympathetic ganglion and its nearby tissue. Sympathetic outflow may be suppressed by directly cooling the ganglion with the stimulator of the present invention until its associated nerve sensitivity and metabolic activities are substantially diminished. In operation, nerve body may be cooled from normal body temperature, about 37° C., preferably down to 5° C., by the present stimulator without permanently damaging the ganglion. Conversely, the stimulator may include thermal means that can heat the sympathetic ganglion in order to excite its associated nerve and metabolic activities. Preferably, the heating may be carried out in the temperature range of 37° C., to 65° C. without permanently damaging the ganglion.

Another embodiment of the present invention involves applying optical irradiation to stimulate targeted sympathetic ganglion. Although electrical stimulation of nerves is quite effective, it comes with complications such as damage caused by the physical contact from the electrodes and the inability to stimulate with absolute precision, thereby causing undesired stimulation of the nearby tissues. Optical energy such as laser allows more controlled and selective spatial resolution of stimulation than electrical stimulation. Laser produces coherent light that has radiation waves that are in alignment with each other and are typically of a single wavelength. To achieve effective optical irradiation, the neurons must be driven at adequate rate to produce safe, reproducible action potentials.

In the present invention, a stimulator equipped with a light source driver and a plurality of diodes may be implanted near the sympathetic ganglion to evoke desired neural activity. Low-level laser diode or light-emitting diodes may be employed. Particularly, low-level, pulsed near infrared laser light may be used to elicit neural activation of the associated sympathetic ganglion. In one embodiment, a pulsed diode laser, with wavelength in the range of 1000 nm to 2000 nm, pulse duration in the range of about 1 ms to about 20 ms and repetition rate in the range of 1 Hz-10 Hz may be used to stimulate the ganglion until symptoms of the associated disorder are alleviated.

The following examples discuss each of the physiological disorders that may be treated by the stimulation method of the present invention by grouping the relevant ganglia associated with the disorder and the preferred parameters of the PRF used.

EXAMPLE 1

PRF stimulation may be applied to treat hyperhidrosis. Patients who are suffering from palmar hyperhidrosis or other forms of hyperhidrosis are found to have abnormal sympathetic activities with the T2 and T3 ganglia.

To treat palmar or axillary hyperhidrosis, the wireless, battery-less and lead-less stimulator is implanted over the inferior stellate ganglion and over upper thoracic ganglia. Preferably, the stimulator is positioned over the T2 and T3 ganglia. A rapid PRF that exceeds the natural cycling rate of the nerve polarization and depolarization (overpacing) is applied to the T2 and T3 ganglia until the nerve and its neurotransmitters are fatigued so that no signals can be further conducted. The PRF should be operated at a frequency of 500 KHz, current amplitude at 5 volts, repetition rate at 2 Hz, and pulse width duration at 50 ms. PSP and PST of the patient are monitored before, during and after PRF stimulation until the symptom of the palmar hyperhidrosis is alleviated.

EXAMPLE 2

Raynaud's phenomenon is a vasospastic disorder triggering discoloration of the fingers, toes and occasionally other areas. The disorder is caused by increased activation of sympathetic noradrenergic nerves controlling muscle tone of digit arteriolar walls.

Treatment of Raynaud's phenomenon is akin to the procedures conducted with patients suffering from palmar hyperhidrosis. PRF stimulation in the form of overpacing is applied to the T2 and T3 ganglia until symptom is improved. Preferably, the PRF should be operated at a frequency of 500 KHz, current amplitude at 5 volts, repetition rate at 2 Hz, and pulse width duration at 50 ms. Temperatures of the fingers are monitored before, during and after the PRF stimulation.

EXAMPLE 3

The cerebral blood vessels, particularly the pial vessels, have an abundance of non-adrenergic sympathetic nerve distribution that originates in the cervical ganglia and follows the carotid artery to project into the ipsilateral hemisphere. The intracerebral vessels constrict when sympathetic nerve is excited and dilated when these fibres are interrupted. Stellate ganglion block has shown to improve cerebral perfusion by reducing the cerebral vascular tone.

The first thoracic sympathetic ganglion fuses with the inferior cervical ganglion to make the stellate ganglion. Stellate ganglion sits at the top end of the sympathetic chain in front of the C7 vertebra of the neck. For the treatment of cerebral ischemia, a wireless, battery-less and lead-less stimulator is surgically implanted over the stellate ganglion. PRF in the form of overpacing is applied to inhibit sympathetic outflow. Preferably, the PRF should be operated at a frequency of 500 KHz, current amplitude at 5 volts, repetition rate at 2 Hz, and pulse width duration at 50 ms. Physiological conditions of the patient, such as heart rate and blood pressure, should be monitored before, during and after the procedure.

EXAMPLE 4

Sympathetic activities of the lower cervical and upper thoracic sympathetic ganglia may affect the tracheal, bronchial, and pulmonary systems. Therefore, proper PRF stimulation of the lower cervical and upper thoracic sympathetic ganglia may be conducted to treat asthma by alleviating the contraction of the smooth muscles of the airways.

Particularly, positioning a PRF stimulator in the proximity of T2 to T4 ganglia may help treating patients suffering from asthma. Adjusting the parameters of the stimulator to drive (increase) sympathetic output has proven to relax the airways. Preferably, the PRF should be operated at a frequency of 500 KHz, current amplitude at 5 volts, repetition rate at 2 Hz, and pulse width duration at 0.1 ms, until the symptom of the asthma has relieved. Physiological conditions of the patient, such as heart rate and blood pressure, should be monitored before, during and after the procedure.

EXAMPLE 5

Untreated hypertension can lead to central nervous complications such as stroke and vascular dementia. Patients suffering from hypertension may be found to have renal disease or abnormal renal function. An effective way to treat hypertension may involve controlling the afferent nerve signals from the kidney to the brain and blocking efferent nerve stimuli from entering the kidney.

A PRF stimulator of the present invention is used for renal denervation to reduce sympathetic nerve outflow. The stimulator is positioned in the proximity of renal artery, preferably in the region of T5 through T12 ganglion. PRF in the form of overpacing is applied to the targeted site until symptom of hypertension is demonstrably improved. Preferably, the PRF should be operated at a frequency of 500 KHz, current amplitude at 5 volts, repetition rate at 2 Hz, and pulse width duration at 50 ms. Systematic blood pressure and heart rate are monitored before, during and after the PRF stimulation.

Conventional electrical stimulator typically comprise a pulse generator capable of producing electric stimulation signals which are sent to targeted nerve by insulated leads coupled to the spinal cord by one or more electrodes. The pulse generator can either be implanted inside the patient or left outside the body. For temporary treatment where the pulse generator is left outside the patient body, an introducer equipped with electrode on the tip is surgically inserted and positioned in the vicinity of the targeted nerve. The proximal end of the introducer is left outside of the body and connected to a pulse generator. For the implanted application, an introducer is used to position the stimulation lead, which is affixed to the targeted tissue and left in place after the introducer is withdrawn. The lead is then connected to the pulse generator that is implanted somewhere in the body. A pulse generator used in the implanted application is usually equipped with a battery for power.

Lead is a device used to access the nerve targeted for stimulation. It is typically a bundle of electrically conducting wires insulated from the surrounding by a non-electrically conducting coating. The wires of the lead connect the pulse generator to the stimulation electrodes, which transfers the energy pulse to the nerve. Leads may be conventional percutaneous leads or paddle-type leads. Depending on the locations of the nerve and the pulse generator, the length of the lead usually ranges from 10 cm to 30 cm. Electrodes are conductive terminals, usually at the end of the lead, that may contact the nerve directly or contact tissues adjacent to the nerve. Electrodes can have different geometric configurations and can induce an electric field that affects the nerve activities. Electrodes are generally made with platinum (pt), gold (Au), titanium (Ti), stainless steel, or alloy.

Figure 6:
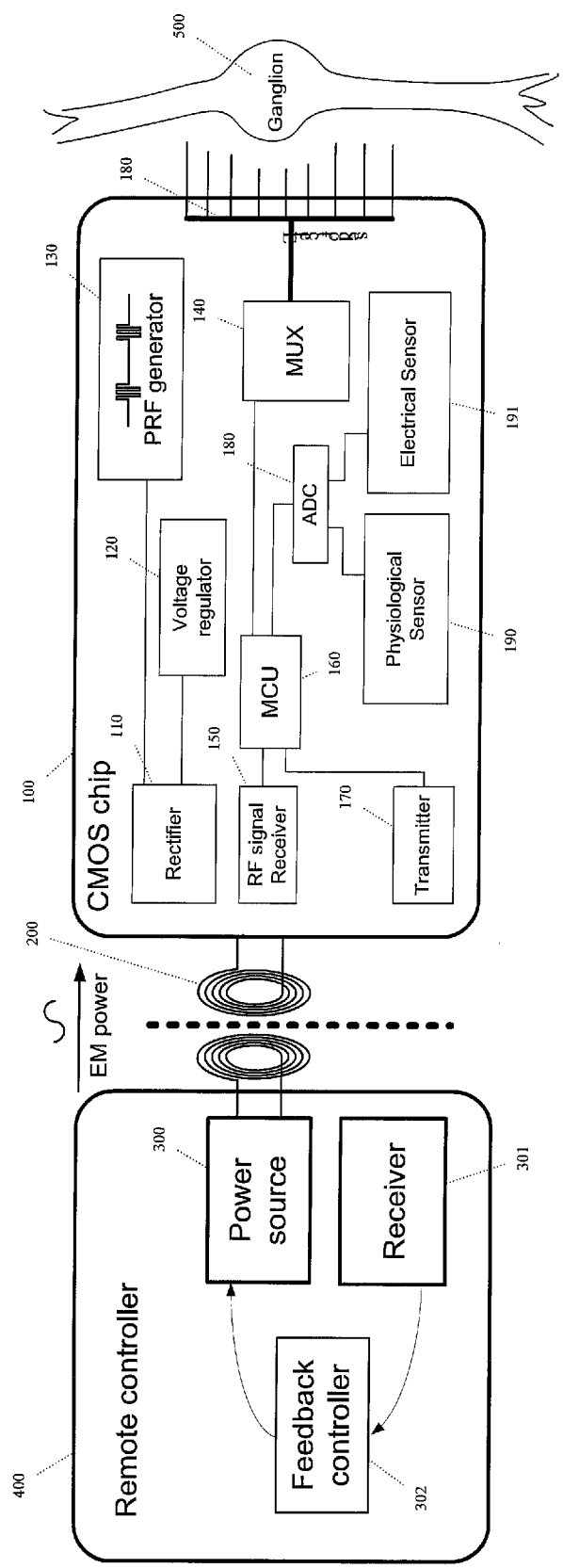
FIG. 6 is a schematic diagram illustrating an implantable stimulator capable of providing pulsed radiofrequency according to an embodiment of the present invention.

The present invention discloses a novel implantable stimulator which is wireless, battery-less and lead-less. FIG. 6 is a schematic diagram illustrating one embodiment of the present invention. As shown in FIG. 6, the stimulator includes a telemetric CMOS chip 100, a coil 200, and a plurality of stimulating electrodes 180. The stimulator is percutaneously implanted in the proximity of the targeted ganglia 500 for PRF stimulation.

The plurality of electrodes 180, the coil 200, and the telemetric CMOS chip 100 are electrically interconnected and housed in one stimulator package. The size of the stimulator, which requires no battery and is implemented using CMOS technology, is no bigger than a microscopic chip. Preferably, the size of the stimulator shall not exceed 5 mm×15 mm. A power source 300, configured within a remote controller 400, wirelessly powers the CMOS chip 100 via the coil 200. Power may be transmitted by inductive coupling or any other wireless charging mechanisms such as electromagnetic induction coupling, resonate inductive coupling, capacitive coupling, light (optical, laser), or radio frequency charging (e.g., 900 MHz band or radio or microwave). A preferred embodiment of the power source 300 may be a Class-E power amplifier, which provides higher power transmission efficiency than other conventional power amplifiers. Generally, high-frequency signals have shorter skin penetration than low-frequency signals. The preferred embodiment here is to use 1 MHz wireless signals to power the CMOS chip 100 of the stimulator.

A remote controller 400, which houses the power source 300, the receiver 301 and the feedback controller 302, is configured to locate outside of patient body and away from the implanted stimulator. In addition to being a wireless power source for the implanted stimulator, the remote controller 400 may also receive signals transmitted from the CMOS chip 100, and vice versa. The remote controller 400 may adjust the stimulation parameters of the PRF based on the received signals and transmit renewed parameter commands to the CMOS chip 100 until the symptoms of the diseases are improved. Note that in the present invention no wire is needed to connect the remote controller 400 with the CMOS chip 100. In one embodiment, the remote controller 400 may locate up to 7 cm from the implanted stimulator. The remote controller 400 may also be implemented in preexisting device such as a mobile phone, a tablet, a laptop computer or any mobile equipment. By configuring the remote controller within a preexisting device, the patient may conveniently control and charge the implanted stimulator without further carrying an additional device Referring to FIG. 6, the CMOS chip 100 may comprise elements such as: rectifier 110, voltage regulator 120, PRF generator 130, multiplexer 140, RF signal receiver 150, micro-controller 160, transmitter 170, analog digital converter 180, physiological sensor 190, and electrical sensor 191.

In operation, wireless power provided by remote controller 400 may be rectified by rectifier 110 to convert the wireless power to direct current. Voltage regulator 120 may regulate the direct current to obtain steady voltage and remove signal noise. Rectifier 110 may also send current directly to the PRF generator to generate pulsed radiofrequency.

The stimulator of the present invention further comprises an electrical sensor means for monitoring the electrical states of the ganglion and the CMOS chip. The electrical sensor 191 may monitor the bio-impedance of the ganglion that is being stimulated. It may also measure the electrical and functional states of the CMOS chip 100, for examples the voltage level, current amplitude, impedance, and chip temperature.

The stimulator of the present invention may further comprise a physiological sensor means for monitoring the physiological states of the patient being treated. The physiological sensor 190 may monitor the tissue and body temperatures, heart rate, blood pressure, blood oxygen level and/or other physiological states of the patient. In one embodiment of the present invention, the physiological sensor 190 may include a measuring means that can clamp or cuff to a blood vessel near the ganglion to allow measurement of the physiological states of the patient. The measuring means may be in any shape or size as long as it can clamp to a blood vessel.

The micro-controller 160 receives the monitored states from the sensors 190 and 191, and may adjust the stimulation parameters of the PRF according to preprogrammed protocols. Stimulation parameters may include: pulse frequency, pulse width duration, current/voltage amplitude, repetition rate, duty cycle and/or waveform. In another embodiment, the monitored states received by the sensors 190 and 191 may be transmitted by transmitter 179 to the receiver 301 of the remote controller 400. The remote controller 400 may adjust the stimulation parameters based on the monitored states and then transmit modulated parameter instructions to the RF signal receiver 150 of the CMOS chip 100. In one embodiment, the remote controller 400 may be configured to display the electrical states of the CMOS chip 100 and the ganglion or the physiological states of the patient for ease of controlling the PRF stimulation parameters.

Figure 7:
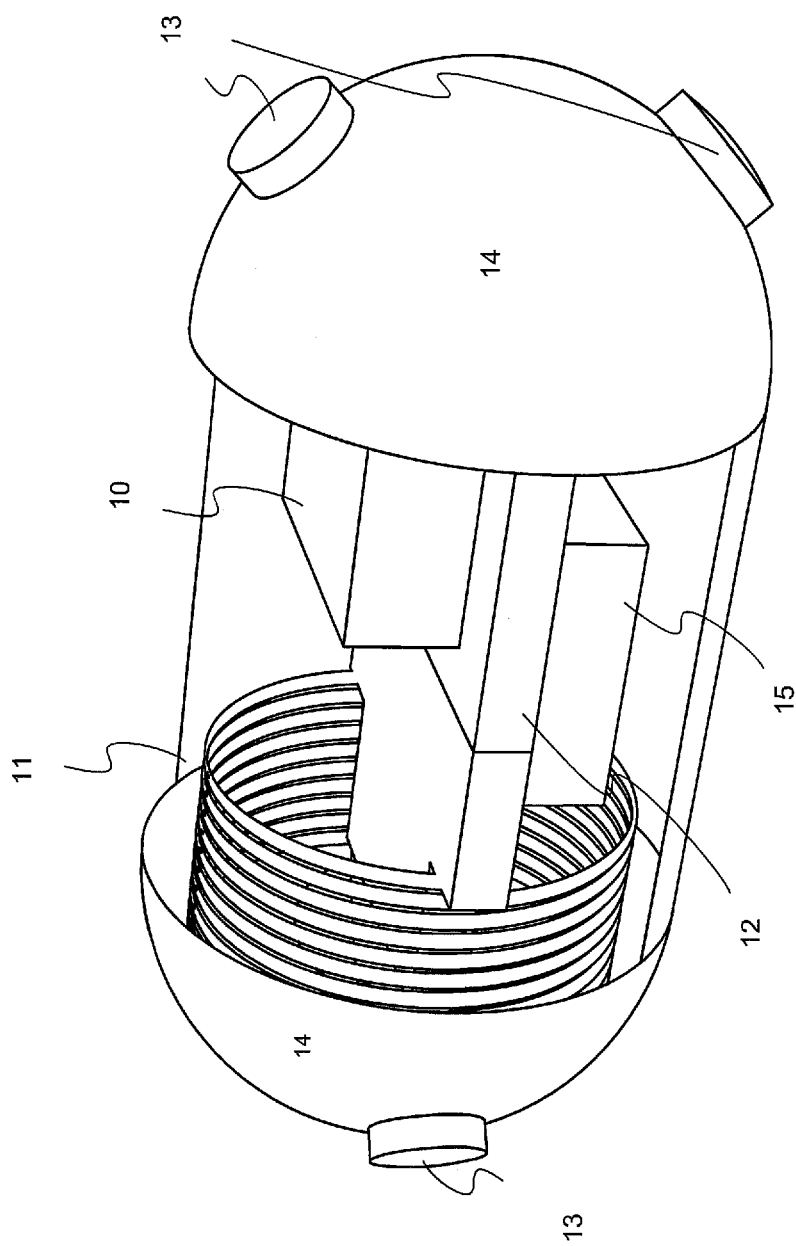
FIG. 7 illustrates an embodiment of the wireless, battery-less and lead-less stimulator in one stand-alone package.

The present invention further teaches an implantable wireless and battery-less stimulator that requires no lead. FIG. 7 illustrates one embodiment of the present invention. This novel stimulator device combines a plurality of electrodes 13, the CMOS chip 10 and the power receiver 11 in one stand-alone package which simplifies the implanting procedure as well as eliminates disturbance of tissues caused by lead. Under the stimulator package 14, the CMOS chip 10 may be placed on a substrate layer 12 support by a component 15. The component 15 may be a capacitor, a thermal source driver, an optical source driver and/or the sensor means. Power receiver 11 may be configured to couple the CMOS chip 10 inside the stimulator package 14 to minimize the stimulator size. The plurality of electrodes 13 may be configured to evenly space apart around the stimulator package 14 or in any fashion that can provide optimal contact with the nerve tissue. On the circuit level, as shown in FIG. 6, the PRF generator 130 of the CMOS chip 100 connects to the electrodes 180 via the multiplexer 140. In structure, the electrodes 13, surrounding the stimulator package 14 without leads, stimulate the targeted ganglion by applying appropriate PRF. The present invention removes the extension leads that connect electrodes with the stimulator in the prior art systems. A complete lead-less system may avoid problems such as lead fracture or lead leakage found in a lead-based system. It can also simplify implant procedure by allowing simple insertion of a single stand-alone stimulator in the proximity of the targeted ganglion without concerning lead anchoring, lead migration or lead disturbance. The stimulator embodiment illustrated in FIG. 7 also may be sutured directly to the nerve or nearby tissues such as pleura.

In another embodiment, the plurality of electrodes may be replaced with a plurality of thermal conductors or optical diodes, depending on the configurations of the CMOS chip inside the stimulator. Note that the shape of the stimulator package is not limited. Any package that can house the CMOS chip, power receiver and the plurality of electrodes/thermal conductors/light diodes in one stand-alone package falls under the scope of the present disclosure.

The stimulator of the present invention may further comprise a fastening means to help secure the stimulator to the nerve or nearby tissues. The fastening means may be in the form of a clamp, claw, cuff or any other configurations to facilitate securing of the stimulator. The fastening means may also be configured as the measuring means for the physiological sensor to help monitoring the physiological states of the patient.

To permit safe implantation, the stimulator may be encapsulated by biomaterials such as polydimethylsiloxane (PDMS) or epoxy-titanium. Coating the stimulator with PDMS or similar materials not only can protect the telemetric CMOS circuit, but also offer enhanced adhesion property to the nerve or nearby tissues.

Figure 8:
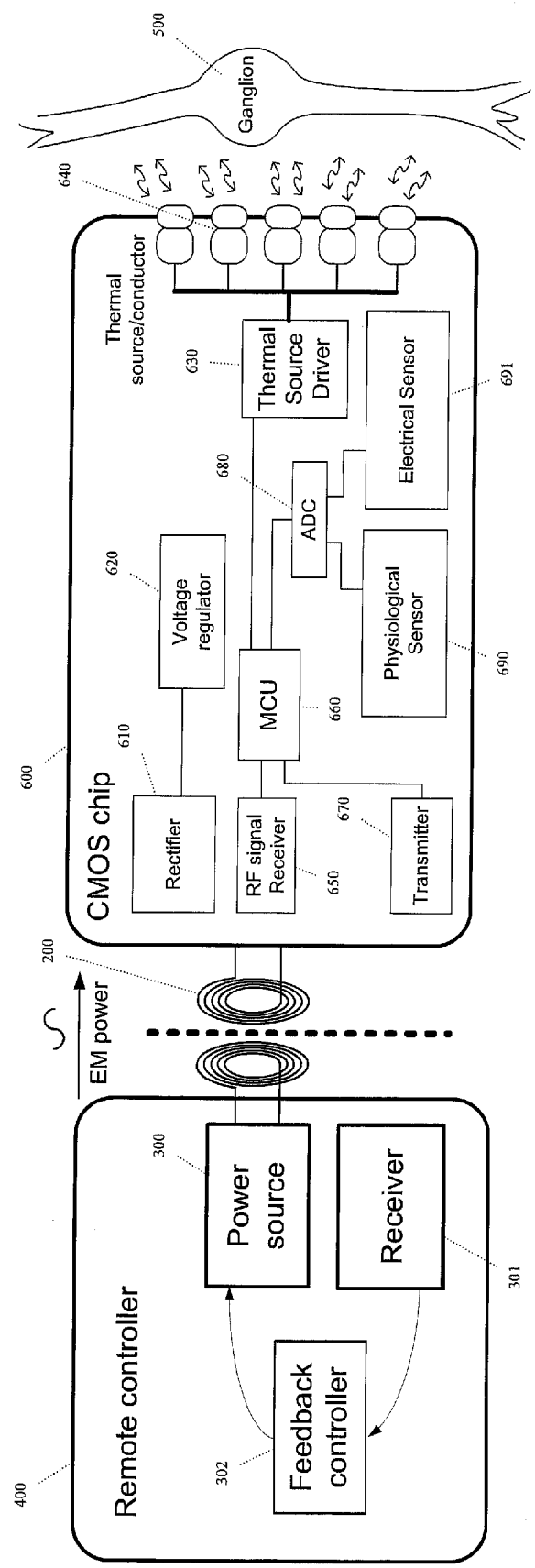
FIG. 8 is a schematic diagram illustrating an implantable stimulator capable of providing thermal energy according to an embodiment of the present invention.

FIG. 8 is another embodiment of the present invention that involves a wireless, battery-less and lead-less stimulator capable of applying thermal energy to stimulate targeted ganglion 500. Such implantable stimulator comprises a CMOS chip 600 that includes: power rectifier 610, voltage regulator 620, thermal source driver 630, thermal source/conductor 640, RF signal receiver 650, micro-controller 660, transmitter 670, analog digital converter 680, physiological sensor 690, and electrical sensor 691. The stimulator is wirelessly powered by power source 300 of remote controller 400 via coil 200. The CMOS chip 600 is configured for bilateral data transmission in which receiver 301 may also receive signals from transmitter 670.

The thermal source driver 630 may convert electrical energy to temperature differentials. Specifically, the thermal source driver 630 may contain a Peltier cell or module that converts electrical voltage to thermal energy. Thermal energy may be in either cooling or heating form. The thermal source driver 630 applies thermal energy to the ganglion 500 via a plurality of thermal conductors 640. Thermal energy is also precisely controlled by the micro-controller 660 to avoid permanently damaging the ganglion.

Figure 9:
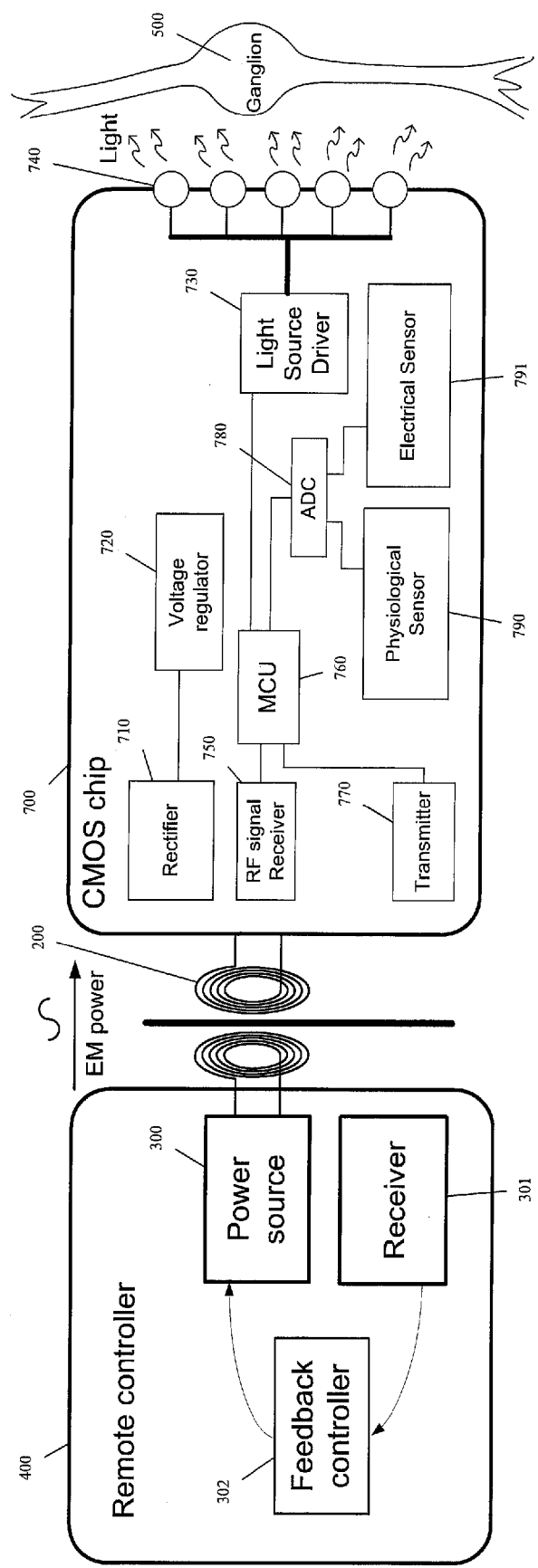
FIG. 9 is a schematic diagram illustrating an implantable stimulator capable of providing thermal optical irradiation to an embodiment of the present invention.

FIG. 9 is yet another embodiment of the present invention that discloses a wireless, battery-less and lead-less stimulator capable of applying optical irradiation to stimulate targeted ganglion 500. The implantable stimulator comprises a CMOS chip 700 that includes: power rectifier 710, voltage regulator 720, light source driver 730, a plurality of diodes 740, RF signal receiver 750, micro-controller 760, transmitter 770, analog digital converter 780, physiological sensor 790, and electrical sensor 791. The stimulator is wirelessly powered by power source 300 of remote controller 400 via coil 200. The CMOS chip 700 is configured for bilateral data transmission in which receiver 301 may also receive signals from transmitter 770.

The light source driver 730 may be a laser diode diver that delivers precise current to the plurality of diodes 740 for optical stimulation of the ganglion. Diode laser is preferred in nerve stimulation because they are small, low-intensity and require relative little power. In one preferred embodiment, a low-power pulsed infrared laser driver may be used to drive the diodes. Other types of light source driver may also be employed in the stimulator of the present invention as long as safe and reproducible nerve action potential can be evoked.

While the invention has been described in connection with what is presently considered to be the most practical and preferred embodiment, it is to be understood that the invention is not to be limited to the disclosed embodiment, but on the contrary, is intended to cover various modifications and equivalents included within the spirit and scope of the appended claims.

What is claimed is:

1. A method for treating a disease of a patient diagnosed with at least one of hyperhidrosis and Raynaud's phenomenon, the method comprising:

positioning an implantable, lead-less and battery-less stimulator proximate to T-2 ganglion and T-3 ganglion along the sympathetic nerve chain wherein the stimulator is configured to be wirelessly controlled and charged;

monitoring the bio impedance of the T-2 ganglion and T-3 ganglion and the electrical states of the stimulator;

transmitting the monitored bio impedance and electrical states to a remote controller;

applying pulsed radiofrequency in a sinusoidal waveform to the T-2 ganglion and T-3 ganglion via the stimulator; and adjusting the stimulation parameters of the pulsed radiofrequency with the remote controller based on the monitored bio impedance and electrical states until the symptoms of the disease have been alleviated.

2. The method of claim 1, wherein the stimulation parameters comprise pulse frequency, pulse width duration, current amplitude, voltage amplitude, duty cycle and waveform of the pulsed radio frequency.

3. The method of claim 1, wherein the electrical states of the stimulator comprise voltage level, current amplitude, impedance and temperature of the stimulator.

4. The method of claim 1, further comprising the step of monitoring the physiological states of the patient.

5. The method of claim 4, wherein the physiological states of the patient comprise heart rate, body and tissue temperatures, blood pressure and blood oxygen level of the patient.

6. The method of claim 4, further comprising the step of adjusting the stimulation parameters of the pulsed radiofrequency based on the monitored physiological states.

7. The method of claim 4, further comprising the step of transmitting the monitored physiological states to the remote controller.

8. The method of claim 7, further comprising the step of adjusting the stimulation parameters of the pulsed radiofrequency with the remote controller based on the monitored physiological states.

9. The method of claim 4, further comprising the step of clamping a measuring means to a blood vessel near the T-2 ganglion and T-3 ganglion along the sympathetic nerve chain.

10. The method of claim 1, further comprising the step of wirelessly control and charge the stimulator with a remote controller.

11. The method of claim 10, wherein the remote controller wirelessly controls and charges the stimulator by near field inductive coupling, electro-magnetic induction coupling, resonate inductive coupling, capacitive coupling, light or radio frequency spectrum charging.

12. The method of claim 1, wherein positioning the stimulator proximate to T-2 ganglion and T-3 ganglion along the sympathetic nerve chain further comprises suturing the stimulator to the T-2 ganglion and T-3 ganglion or its nearby tissues.

13. The method of claim 1, wherein the pulsed radiofrequency is applied between about 10 KHz to about 10 MHz.

14. The method of claim 1, wherein the pulse radiofrequency amplitude is applied between about 1 volt to about 60 volts.

15. The method of claim 1, wherein the pulse radiofrequency width is applied between about 0.1 microseconds to about 500 microseconds.

* * * * *